United States Patent
Justis et al.

(10) Patent No.: US 7,695,475 B2
(45) Date of Patent: Apr. 13, 2010

(54) INSTRUMENTS FOR MINIMALLY INVASIVE STABILIZATION OF BONY STRUCTURES

(75) Inventors: Jeff R. Justis, Collierville, TN (US); Jonathan Dewey, Memphis, TN (US)

(73) Assignee: Warsaw Orthopedic, Inc.

( * ) Notice: Subject to any disclaimer, the term of this patent is extended or adjusted under 35 U.S.C. 154(b) by 969 days.

(21) Appl. No.: 11/213,473

(22) Filed: Aug. 26, 2005

(65) Prior Publication Data

US 2007/0049931 A1    Mar. 1, 2007

(51) Int. Cl.
    *A61F 5/00* (2006.01)
(52) U.S. Cl. .................. 606/86 A; 606/99; 606/914; 606/250
(58) Field of Classification Search ............ 606/86 A, 606/916, 103, 104, 305, 301, 286, 287, 288, 606/289, 290, 291, 90, 99, 250–279; 623/17.11
    See application file for complete search history.

(56) References Cited

U.S. PATENT DOCUMENTS

| | | |
|---|---|---|
| 2,338,159 A | 1/1944 | Appleton |
| 2,697,433 A | 12/1954 | Zehnder |
| 3,892,232 A | 7/1975 | Neufeld |
| 4,335,715 A | 6/1982 | Kirkley |
| 4,409,968 A | 10/1983 | Drummond |
| 4,448,191 A | 5/1984 | Rodnyansky et al. |
| 4,545,374 A | 10/1985 | Jacobson |
| 4,573,448 A | 3/1986 | Kambin |
| 4,722,331 A | 2/1988 | Fox |
| 4,863,430 A | 9/1989 | Klyce et al. |
| 4,883,048 A | 11/1989 | Purnell et al. |
| 4,896,661 A | 1/1990 | Bogert et al. |
| 4,955,885 A | 9/1990 | Meyers |
| 4,957,495 A | 9/1990 | Kluger |
| 5,020,519 A | 6/1991 | Hayes et al. |
| 5,080,662 A | 1/1992 | Paul |
| 5,116,344 A | 5/1992 | Sundqvist |
| 5,163,940 A | 11/1992 | Bourque et al. |
| 5,171,279 A | 12/1992 | Mathews |
| 5,196,013 A | 3/1993 | Harms et al. |
| 5,242,443 A | 9/1993 | Kambin |
| 5,242,444 A | 9/1993 | MacMillan |
| 5,281,223 A | 1/1994 | Ray |
| 5,314,429 A | 5/1994 | Goble |
| 5,334,205 A | 8/1994 | Cain |
| 5,383,454 A | 1/1995 | Bucholz |
| 5,409,488 A | 4/1995 | Ulrich |
| 5,437,667 A | 8/1995 | Papierski et al. |
| 5,474,551 A | 12/1995 | Finn et al. |
| 5,569,248 A | 10/1996 | Mathews |

(Continued)

FOREIGN PATENT DOCUMENTS

DE    197 26 754 A1    6/1997

(Continued)

*Primary Examiner*—Eduardo C Robert
*Assistant Examiner*—Jan Christopher Merene

(57) ABSTRACT

Systems for positioning a connecting element adjacent the spinal column in minimally invasive procedures include installation instruments that guide the connecting element from a location remote from one or more anchors to a location proximate to the one or more anchors. The installation instruments include extensions mountable to anchors engageable to the spinal column or other bony structure, and inserters mountable to the anchor extensions for positioning the connecting element adjacent the anchors.

9 Claims, 15 Drawing Sheets

U.S. PATENT DOCUMENTS

| | | | |
|---|---|---|---|
| 5,591,165 A | 1/1997 | Jackson | |
| 5,591,167 A | 1/1997 | Laurain et al. | |
| 5,601,562 A | 2/1997 | Wolf et al. | |
| 5,613,968 A | 3/1997 | Lin | |
| 5,613,971 A | 3/1997 | Lower et al. | |
| 5,643,273 A | 7/1997 | Clark | |
| 5,672,175 A | 9/1997 | Martin | |
| 5,681,320 A | 10/1997 | McGuire | |
| 5,683,392 A | 11/1997 | Richelsoph et al. | |
| 5,704,937 A | 1/1998 | Martin | |
| 5,720,751 A | 2/1998 | Jackson | |
| 5,725,532 A | 3/1998 | Shoemaker | |
| 5,735,857 A | 4/1998 | Lane | |
| 5,741,266 A | 4/1998 | Moran et al. | |
| 5,752,962 A | 5/1998 | D'Urso | |
| 5,772,594 A | 6/1998 | Barrick | |
| 5,851,183 A | 12/1998 | Bucholz | |
| 5,871,445 A | 2/1999 | Bucholz | |
| 5,891,034 A | 4/1999 | Bucholz | |
| 5,891,150 A | 4/1999 | Chan | |
| 5,891,158 A | 4/1999 | Manwaring et al. | |
| RE36,221 E | 6/1999 | Breard et al. | |
| 5,910,141 A | 6/1999 | Morrison et al. | |
| 5,941,885 A | 8/1999 | Jackson | |
| 6,036,692 A | 3/2000 | Burel et al. | |
| 6,099,528 A | 8/2000 | Saurat | |
| 6,123,707 A | 9/2000 | Wagner | |
| 6,139,549 A | 10/2000 | Keller | |
| 6,146,386 A | 11/2000 | Blackman et al. | |
| 6,183,472 B1 | 2/2001 | Lutz | |
| 6,226,548 B1 | 5/2001 | Foley et al. | |
| 6,235,028 B1 | 5/2001 | Brumfield et al. | |
| 6,251,111 B1* | 6/2001 | Barker et al. | 606/86 A |
| 6,485,491 B1 | 11/2002 | Farris et al. | |
| 6,530,926 B1 | 3/2003 | Davison | |
| 6,530,929 B1 | 3/2003 | Justis et al. | |
| 6,660,006 B2 | 12/2003 | Markworth et al. | |
| 6,740,089 B2 | 5/2004 | Haider | |
| 6,821,277 B2 | 11/2004 | Teltelbaum | |
| 7,156,849 B2 | 1/2007 | Dunbar et al. | |
| 7,160,300 B2* | 1/2007 | Jackson | 606/273 |
| 7,179,261 B2 | 2/2007 | Sicvol et al. | |
| 7,188,626 B2* | 3/2007 | Foley et al. | 128/898 |
| 2002/0045904 A1 | 4/2002 | Fuss et al. | |
| 2002/0161368 A1 | 10/2002 | Foley et al. | |
| 2003/0060826 A1 | 3/2003 | Foley et al. | |
| 2003/0199884 A1 | 10/2003 | Davison et al. | |
| 2003/0225408 A1 | 12/2003 | Nichols et al. | |
| 2003/0229347 A1 | 12/2003 | Sherman et al. | |
| 2004/0039384 A1 | 2/2004 | Boehm, Jr. et al. | |
| 2004/0138662 A1 | 7/2004 | Landry et al. | |
| 2004/0147937 A1* | 7/2004 | Dunbar et al. | 606/99 |
| 2004/0215190 A1 | 10/2004 | Nguyen et al. | |
| 2004/0267275 A1 | 12/2004 | Cournoyer et al. | |
| 2005/0010221 A1 | 1/2005 | Dalton | |
| 2005/0021031 A1 | 1/2005 | Foley et al. | |
| 2005/0021040 A1 | 1/2005 | Bertagnoli | |
| 2005/0033299 A1 | 2/2005 | Shluzas | |
| 2005/0070917 A1* | 3/2005 | Justis | 606/104 |
| 2005/0080418 A1 | 4/2005 | Simonson et al. | |
| 2005/0085813 A1 | 4/2005 | Spitler et al. | |
| 2005/0131408 A1* | 6/2005 | Sicvol et al. | 606/61 |
| 2005/0131421 A1 | 6/2005 | Anderson et al. | |
| 2005/0154389 A1 | 7/2005 | Selover et al. | |
| 2005/0171540 A1 | 8/2005 | Lim et al. | |
| 2005/0182407 A1 | 8/2005 | Dalton | |
| 2005/0192579 A1 | 9/2005 | Jackson | |
| 2005/0192589 A1 | 9/2005 | Raymond et al. | |
| 2005/0277934 A1 | 12/2005 | Vardiman | |
| 2007/0078460 A1 | 4/2007 | Frigg et al. | |
| 2007/0213714 A1 | 9/2007 | Justis | |

FOREIGN PATENT DOCUMENTS

| | | |
|---|---|---|
| DE | 100 27988 | 1/2002 |
| SU | 0839513 | 6/1981 |
| WO | WO 97/30666 | 8/1997 |
| WO | WO 97/38639 | 10/1997 |
| WO | WO 99/15097 | 4/1999 |
| WO | WO 99/26549 | 6/1999 |
| WO | WO 00/44288 | 8/2000 |

* cited by examiner

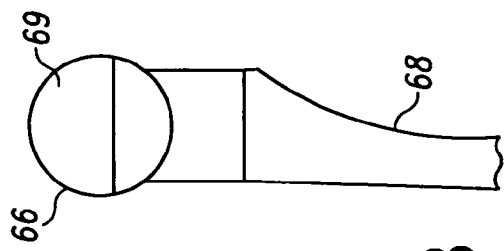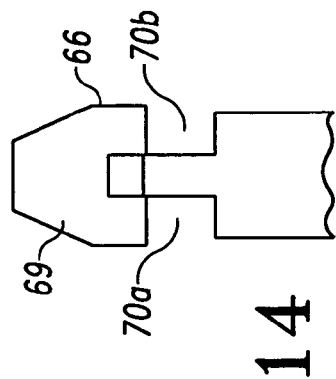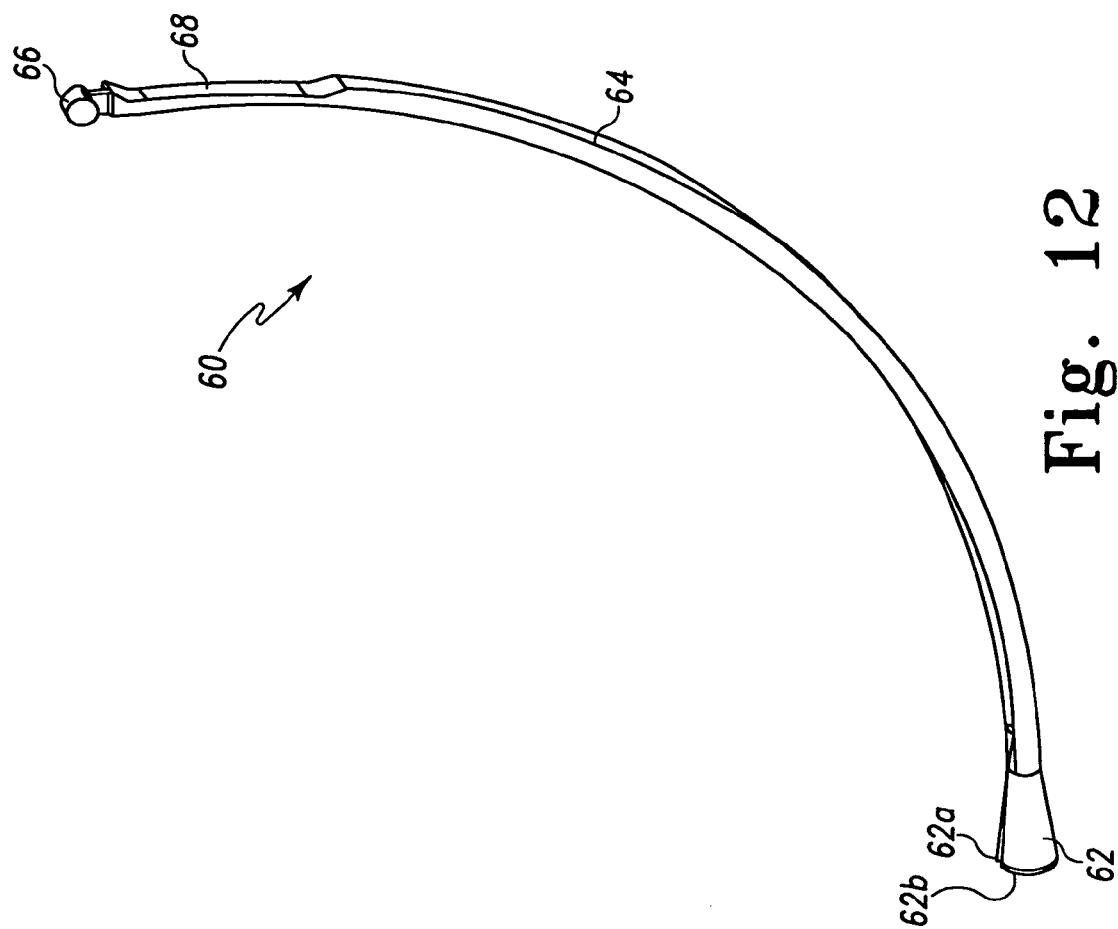

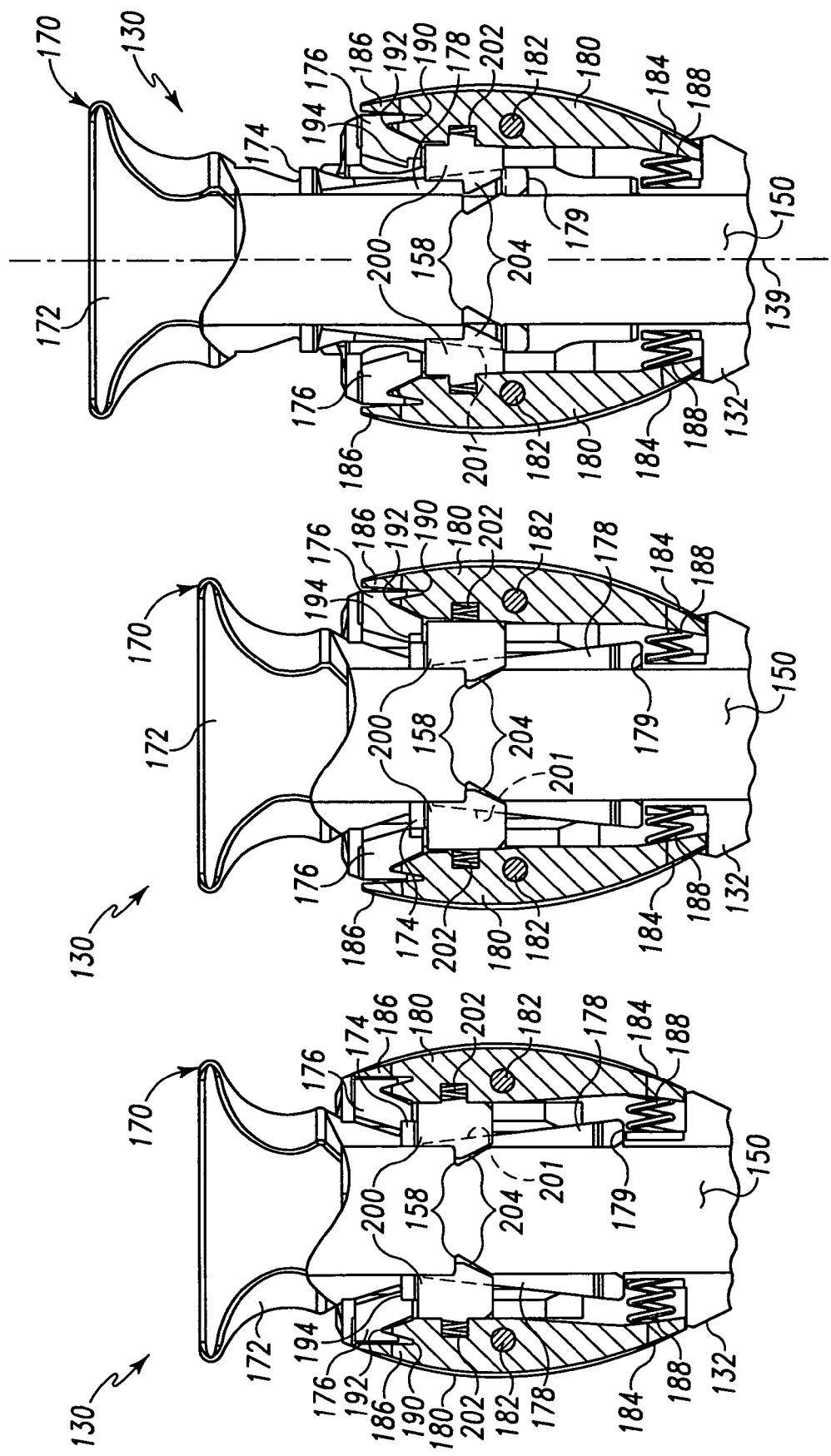

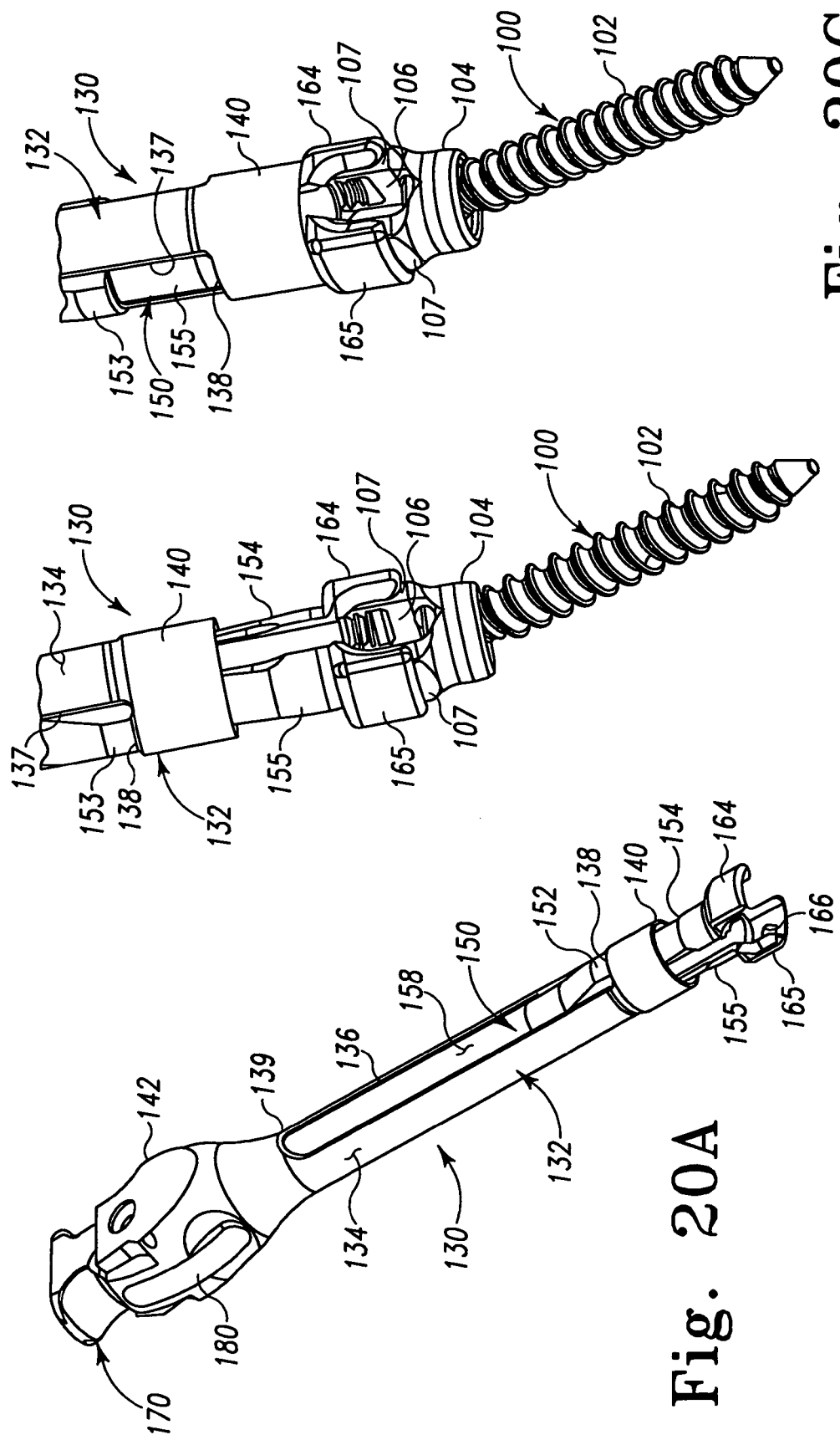

INSTRUMENTS FOR MINIMALLY INVASIVE STABILIZATION OF BONY STRUCTURES

BACKGROUND

Various devices and methods for stabilizing bone structures have been used for many years. For example, the fracture of an elongated bone, such as a femur or humerus, can be stabilized by securing a plate to the fractured bone across the fracture. The plate extends across the fractured area and thus stabilizes the fractured components of the bones relative to one another in a desired position. When the fracture heals, the plate can be removed or left in place, depending on the type of plate that is used.

Another type of stabilization technique uses one or more elongated rods extending between components of a bony structure and secured to the bony structure to stabilize the components relative to one another. The components of the bony structure are exposed and one or more bone engaging fasteners are placed into each component. The elongated rod is then secured to the bone engaging fasteners in order to stabilize the components of the bony structure.

One problem associated with the above described stabilization structures is that the skin and tissue surrounding the surgical site must be cut, removed, and/or repositioned in order for the surgeon to access the location where the stabilization device is to be installed. This repositioning of tissue causes trauma, damage, and scarring to the tissue. There are also risks that the tissue will become infected and that a long recovery time will be required after surgery for the tissue to heal.

Minimally invasive surgical techniques are particularly desirable in, for example, spinal and neurosurgical applications because of the need for access to locations deep within the body and the presence of vital intervening tissues. The development of percutaneous minimally invasive spinal procedures has yielded a major improvement in reducing recovery time and post-operative pain because they require minimal, if any, muscle dissection and can be performed under local anesthesia. These benefits of minimally invasive techniques have also found application in surgeries for other locations in the body where it is desirable to minimize tissue disruption and trauma. There remains a need for further improvements instruments and methods for stabilizing bony structures using minimally invasive techniques.

SUMMARY

Systems for positioning a connecting element adjacent the spinal column in minimally invasive surgical procedures includes an installation instrument with one or more anchor extensions removably engaged to one or more anchors engageable to the spinal column and an inserter movably mounted to the anchor extensions. The inserter is operable to position a connecting element engaged thereto to a location adjacent the one or more anchors in a minimally invasive surgical procedure.

In one form, a single instrument is readily adaptable for spinal stabilization and other procedures employing varying numbers of anchor extensions.

In another form, the installation instrument includes a quick-release actuating mechanism that allows a connecting element to be conveniently and remotely engaged and disengaged to an inserter instrument.

In a further form, the installation instrument includes an inserter arm with a securing member for securing a connecting element thereto. The securing member can be conveniently disassembled from and reassembled with the inserter arm to facilitate cleaning and repair of the installation instrument.

In another form, the installation instrument includes one or more anchor extensions having a toggle mechanism that facilitates engagement and disengagement of the anchor extension to an anchor.

Related features, aspects, embodiments, objects and advantages of the present invention will be apparent from the following description.

BRIEF DESCRIPTION OF THE DRAWINGS

FIG. 12 is a perspective view of a securing member comprising a portion of the inserter.

FIG. 13 is an enlarged elevation view of an upper end of the securing member of FIG. 12.

FIG. 14 is a view looking at a side of the upper end from its FIG. 13 orientation.

FIGS. 19A-19C are elevation views in partial section of a proximal portion of the anchor extension of FIG. 18 showing various positions of a toggle mechanism for securing inner and outer sleeves of the extension in various positions relative to one another.

FIGS. 20A-20C are perspective views showing the anchor extension being secured to an anchor.

DESCRIPTION OF THE ILLUSTRATED EMBODIMENTS

Figure 1:
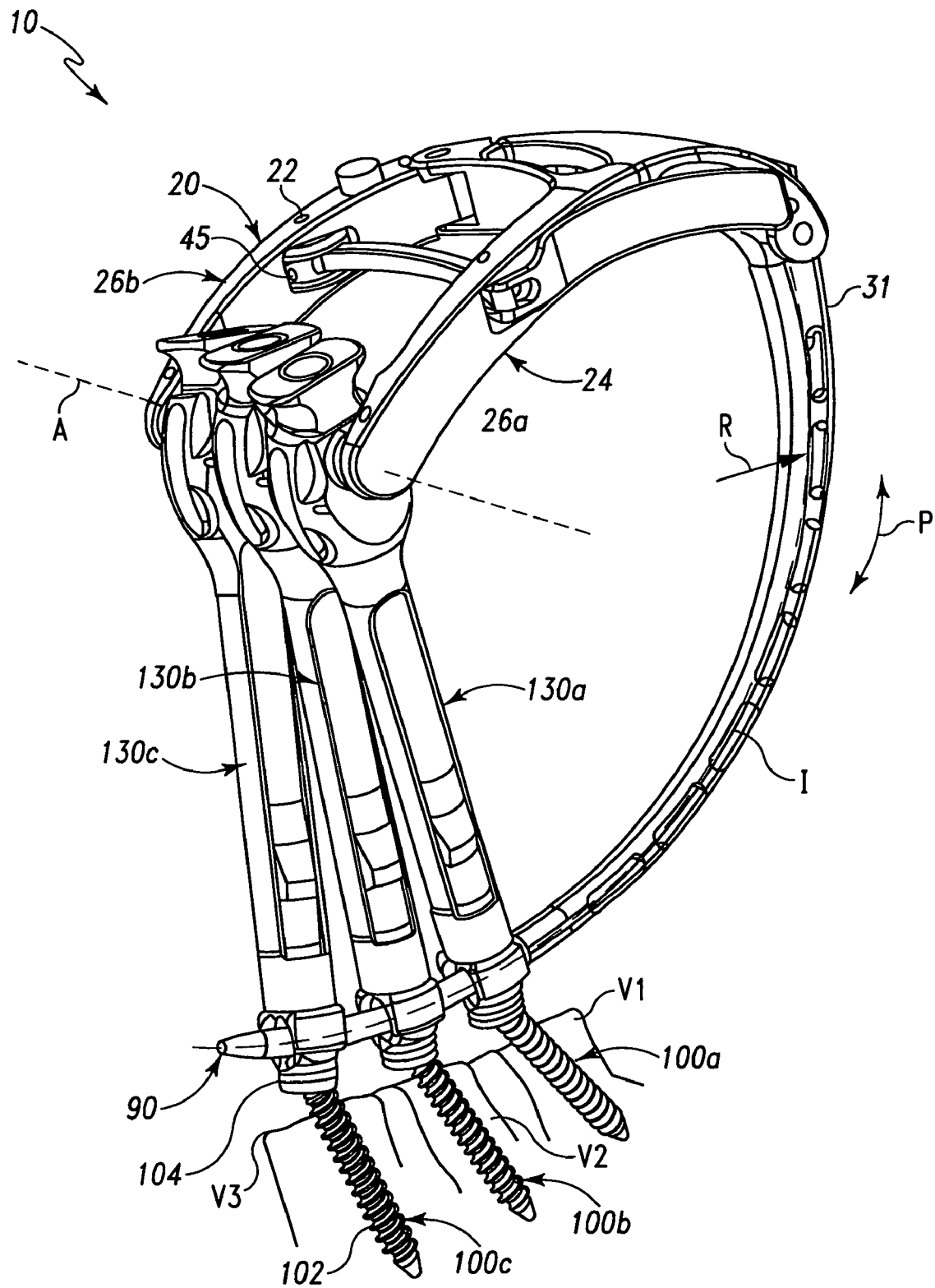
FIG. 1 is a perspective view of a system for positioning a connecting element in a patient in minimally invasive surgical procedures.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Systems and methods for insertion of a connecting element for connection with anchors engaged to bony parts of the body are provided. In one form, the systems include at least one anchor extension extending from at least one anchor engaged to the bony part of the body. An installation instrument is mountable to the at least one anchor extension and operable to position a connecting element from a location remotely positioned from the at least one anchor to a location adjacent to or within the anchor where the connecting element can be secured to the anchor. The anchor and connecting element can each be positioned into the patient in minimally invasive procedures, minimizing trauma and surgical risks to the patient and promoting rapid post-operative recovery. However, applications in non-minimally invasive surgeries are also contemplated.

In another form, the systems include an installation instrument mountable to at least one extension extending from an anchor engaged to the spinal column or other anatomical structure in a patient. The installation instrument is movable relative to the anchor extension to position a connecting element adjacent to the anchor in a minimally invasive procedure. The installation instrument includes a quick-release coupling mechanism for remotely engaging and disengaging the connecting element to the installation instrument.

In a further form, the systems include an installation instrument mountable to at least one extension extending from an anchor engaged to the spinal column or other anatomical structure in a patient. The installation instrument is movable relative to the anchor extension to position a connecting element adjacent to the anchor in a minimally invasive procedure. The installation instrument includes a connecting element securing mechanism that can be readily disassembled from and assembled to the installation instrument for sterilization and/or replacement.

In another form, the systems include an installation instrument mountable to at least one extension extending from an anchor engaged to the spinal column or other anatomical structure in a patient. The installation instrument is movable relative to the anchor extension to position a connecting element adjacent to the anchor in a minimally invasive procedure. The installation instrument includes a mounting portion that is readily adaptable to engage one, two, three or more anchor extensions therebetween depending on the number of anchors employed in the procedure.

In yet another form, the systems include an installation instrument mountable to at least one extension extending from an anchor engaged to the spinal column or other anatomical structure in a patient. The installation instrument is movable relative to the anchor extension to position a connecting element adjacent to the anchor in a minimally invasive procedure. The at least one anchor extensions include a toggle mechanism that is structured to provide rapid and reliable remote engagement and disengagement of an anchor to a distal end of the anchor extension.

Referring now to FIG. 1, there is shown a minimally invasive surgical system 10 that includes an installation instrument 20, three anchor extensions 130a, 130b, 130c, (collectively and individually referred to herein as anchor extensions 130) and a connecting element 90. Anchor extensions 130a, 130b, 130c are releasably mountable to respective ones of the anchors 100a, 100b, 100c (collectively and individually also referred to herein as anchor 100.) Installation instrument 20 is movable about a pivot axis A defined at a coupling location with the anchor extensions 130. Movement of installation instrument 20 swings inserter arm 31 along an arcuate insertion path P defined by insertion axis I. In the illustrated embodiment, path P is defined by a radius R extending to insertion axis I from pivot axis A.

Connecting element or brace 90 can be an elongated rod or shaft curved along its length with a radius of curvature that corresponds generally to the radius of curvature of inserter arm 31. However, it should be understood that it is contemplated that connecting element 90 can include any configuration known for a rod, implant, or fastener, so long as connecting element 90 is insertable using installation instrument 20. Further, connecting element 90 can be non-rigid, elastic and/or super-elastic and in the form of a cable, band, wire, or artificial ligament that used in tethering, guiding, or other surgical procedures. Connecting element 90 can be percutaneously or non-percutaneously inserted with installation instrument 20 to a location adjacent connecting element engaging portions of one or more anchors engaged to a bony structure in the body of an animal subject to stabilize the bony structure.

In the illustrated embodiment, connecting element 90 is a rigid rod curved along an arc that forms an extension of insertion axis I defined by inserter arm 31. However, it is contemplated that connecting element 90 can have a curvature that differs from the curvature of insertion axis I, or can have a curvature that varies or is compounded along its length, or can be linear. The curvature of connecting element 90 and insertion axis I can be configured to define an insertion axis by any one or any combination of mathematical relationships, including, for example, linear, exponential, logarithmic, trigonometric, geometric, parabolic, quadratic, cubic, hyperbolic, elliptic, or parametric relationships, and installation instrument 20 can be adapted or structured to provide insertion along any such insertion pathway. Connecting element 90 in FIG. 1 is inserted via the installation instrument 20 to a location adjacent anchors 100 in order to stabilize the respective vertebrae V1, V2 and V3. The installation instrument 20 can employ any type of fixed geometric relationship to insert connecting element 90 into the patient. This fixed geometric relationship can be governed any one or combination of a pinned joint, a cam, a four-bar linkage, a guide member that provides a path for translational movement of connecting element 90, or any other mechanical relationship that would occur to those skilled in the art.

Anchors 100 include a bone engaging portion 102 and a connecting element engaging portion 104. In the illustrated embodiment, bone engaging portion 102 is a bone screw with a threaded shank to engage the bony structure of the underlying vertebrae. Connecting element engaging portion 104 is a receiver having a pair of opposing arms defining a longitudinal passage alignable along insertion axis I. The arms further define a proximal/distally extending opening that opens at a proximal end of the arms to receiver a set screw (not shown) to secure connecting element 90 in the passage. Bone engaging portion 102 can be pivotally received in connecting element engaging portion 104 through the distal opening thereof, and structured to interact therewith to provide anchor 100 with multi-axial capabilities that permits either a selected number of positions or infinitely numbered of positions of bone engaging portion 102 relative to connecting element engaging portion 104.

Other forms for anchors 100 are contemplated, including uni-axial and uni-planar forms. The bone engaging portion can be in the form of a spike, staple, fusion device, cannulated screw, fenestrated screw, interbody device, intrabody device, clamp, plate, suture anchor, bolt, pin or other bone engaging member. The connecting element engaging portion can be in the form of a saddle, yoke, eye-bolt or through-hole, side opening member, bottom opening member, top-opening member, eyelet, or any other structure engageable to the connecting element.

Figure 3:
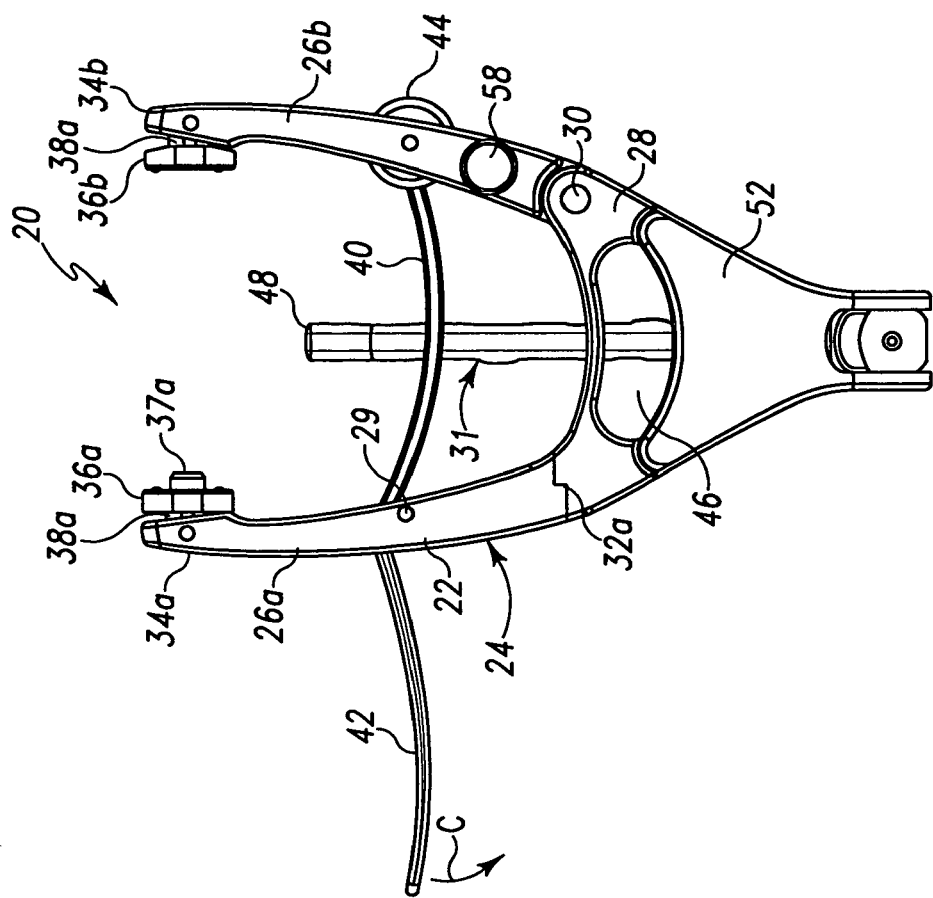
FIG. 3 is a top plan view of the inserter of FIG. 2.
Figure 2:
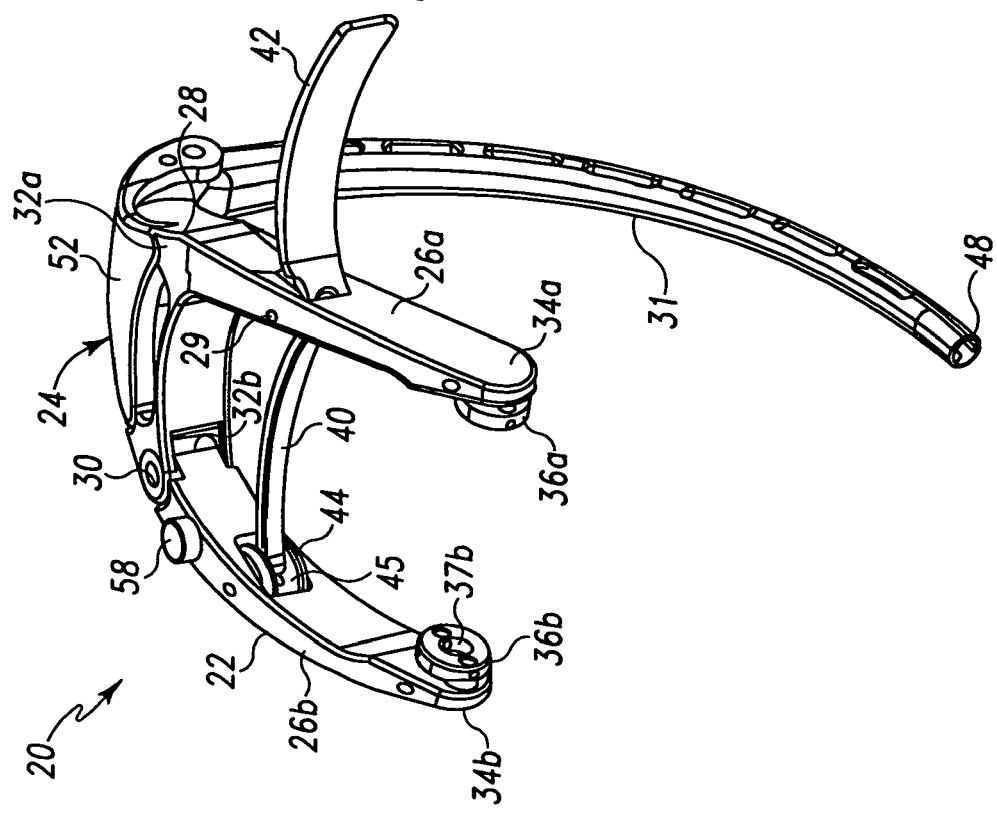
FIG. 2 is a perspective view of an inserter of the system of FIG. 1 in an open condition.

Referring now further to FIGS. 2-3, there is shown an inserter 24 of installation instrument 20 in an open condition and without anchor extensions 130 or brace 90. Inserter 24 includes inserter arm 31 extending from a mounting portion 22. Mounting portion 22 includes a pair of support arms 26a, 26b that extend from proximal end portions of anchor extensions 130 when mounted thereto. Support arms 26a, 26b extend to a junction portion 28, providing mounting portion 22 with a general U or V-shape when viewed from above (FIG. 3.) When viewed from the side (FIG. 7), support arms 26a, 26b include an upward or proximally oriented convex curvature. Inserter arm 31 extends from junction portion 28 along insertion axis I, and is oriented transversely to support arms 26a, 26b.

First support arm 26a is fixed relative to junction portion 28 at fixed end 32a. Junction portion 28 extends from first support arm 26a to coupling portion 30 adjacent second support arm 26b. Second support arm 26b includes a pivot end 32b received in coupling portion 30 and pivotally secured thereto with a pin, living hinge, or other suitable pivotal coupling arrangement. Second support arm 26b extends from pivot end 32b to an anchor extension engaging end 34b. First support arm 26a extends from fixed end 32a to an anchor extension engaging end 34a. Engaging ends 34a, 34b each include an extension engaging member 36a, 36b, respectively. Engaging members 36a, 36b are pivotally mounted on respective ones of posts 38a, 38b extending from support arms 26a, 26b, and are positioned to face one another between support arms 26a, 26b. Engaging member 36a includes a mounting pin 37a projecting therefrom, and engaging member 36b includes a mounting receptacle 37b extending therein. Other arrangements contemplate that each of the engaging members 36a, 36b includes a mounting pin, or that each includes a mounting receptacle.

First support arm 26a is joined to second support arm 26b with a clamping assembly. The clamping assembly includes a pivotal clamping arm 40 extending between support arms 26a, 26b. Clamping arm 40 is pivotally connected at a first end to a lever 42. Lever 42 is further pivotally coupled to support arm 26a with a pin 29 offset from its pivotal connecting with clamping arm 40 to allow translation of clamping arm 40 relative to support arm 26a. Clamping arm 40 is pivotally connected at its second end to a wheel 44. Wheel 44 is rotatably mounted to second support arm 26b, and includes a circumferential opening 45 extend partly therearound through which clamping arm 40 extends. The second end of clamping arm 40 is coupled to wheel 44 at a location spaced radially from the rotational center of wheel 44. A release mechanism 58 engages wheel 44 to maintain wheel 44 in a desired rotational position relative to support arm 26b.

Figure 4:
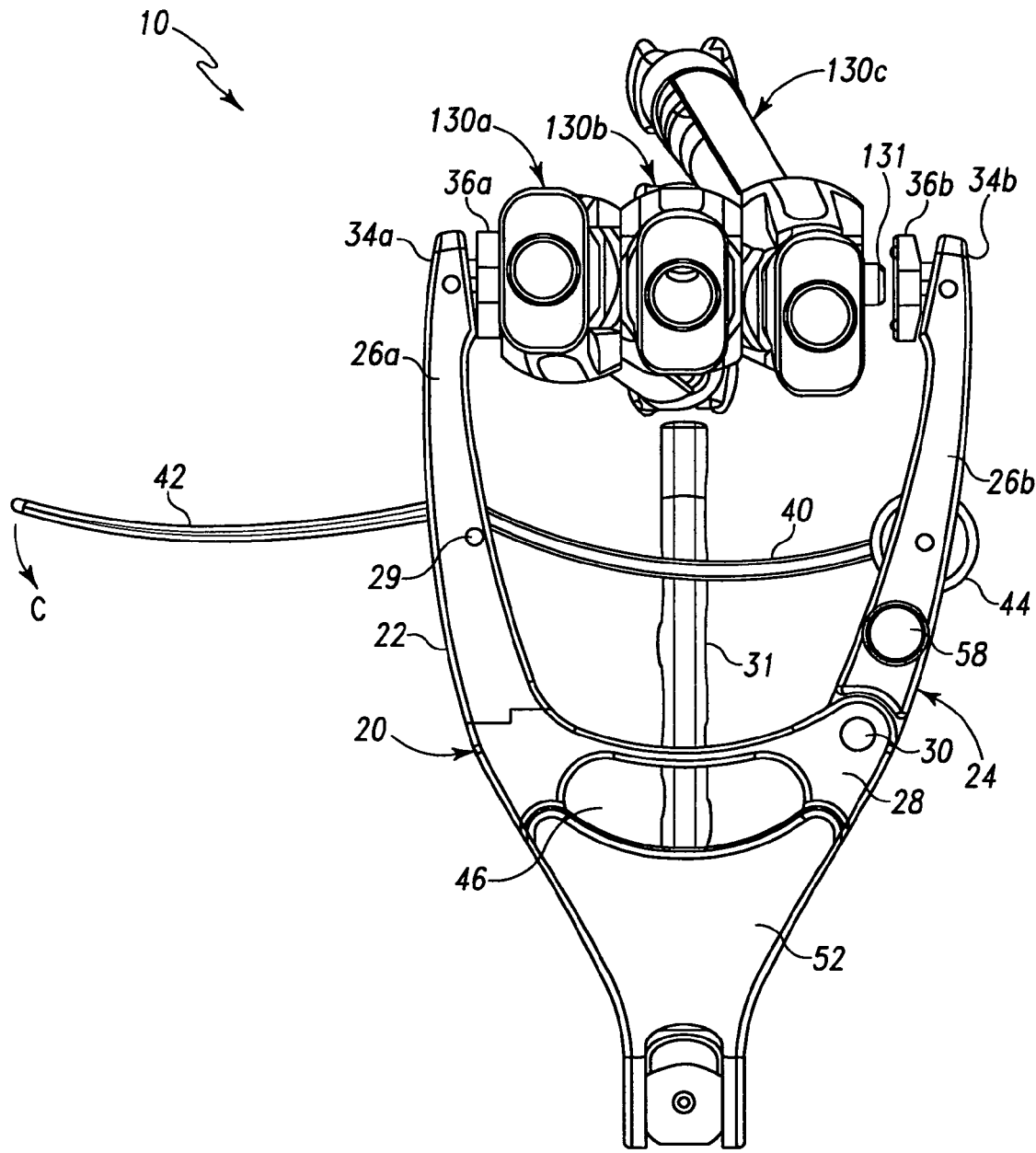
FIG. 4 is the view of FIG. 3 with three anchor extensions positioned between open support arms of the inserter.
Figure 5:
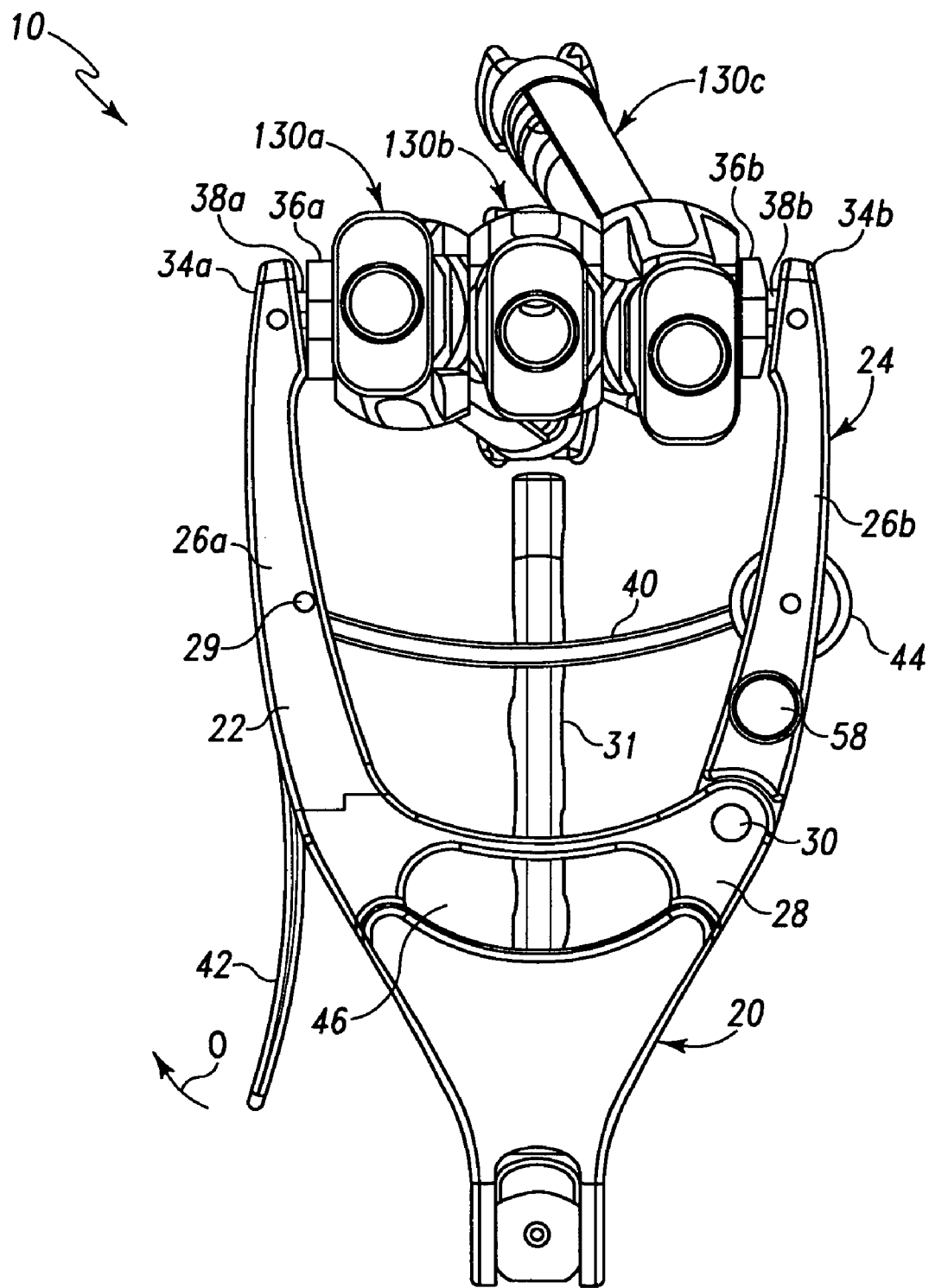
FIG. 5 is the view of FIG. 4 with the support arms of the inserter clamped to the anchor extensions.

When support arms 26a, 26b are moved toward their clamping position, as shown in FIGS. 4-5, second support arm 26b is pivoted toward first support arm 26a against the bias of clamping arm 40 to bring anchor engaging ends 34a, 34b toward one another. Mounting pin 37a is rotatably received in a receptacle (not shown) of anchor extension 130c, while mounting receptacle 37b rotatably receives a pin 131 extending from anchor extension 130c. The toggling capabilities of engaging members 36a, 36b permits the pins and receptacles to self-align with one another as the clamping force is applied to anchor extensions 130 to ensure a rotatable connecting between inserter 24 and the anchors extensions 130. Inserter 24 is thus pivotally mounted to the anchor extensions 130 and movable relative thereto deliver the connecting element from a remote location to a location more proximate the anchors 100, as shown in FIG. 1.

Clamping arm 40 is pivotally coupled to lever 42 so that movement of lever 42, as indicated by arrow C (FIGS. 3, 4) toward a closed position, shown in FIG. 5, translates the first end of clamping arm 40 relative to first support arm 26a as arms 26a, 26b are moved toward one another to secure extensions 130 therebetween. Lever 42 can be pivoted until it is flush alongside first arm 26a. The bowed clamping arm 40 pushes against the first end of lever 42 to bias it to the closed position as viewed in FIG. 5. This provides a firm locked, rotational engagement of the support arms 26a, 26b to anchor extensions 130. As shown in FIG. 5, lever 42 can be moved in the direction of arrow O against the bias of clamping arm 40 to allow support arms 26a, 26b to move away from one another a sufficient distance to release the anchor extensions 130 from therebetween.

Figure 6:
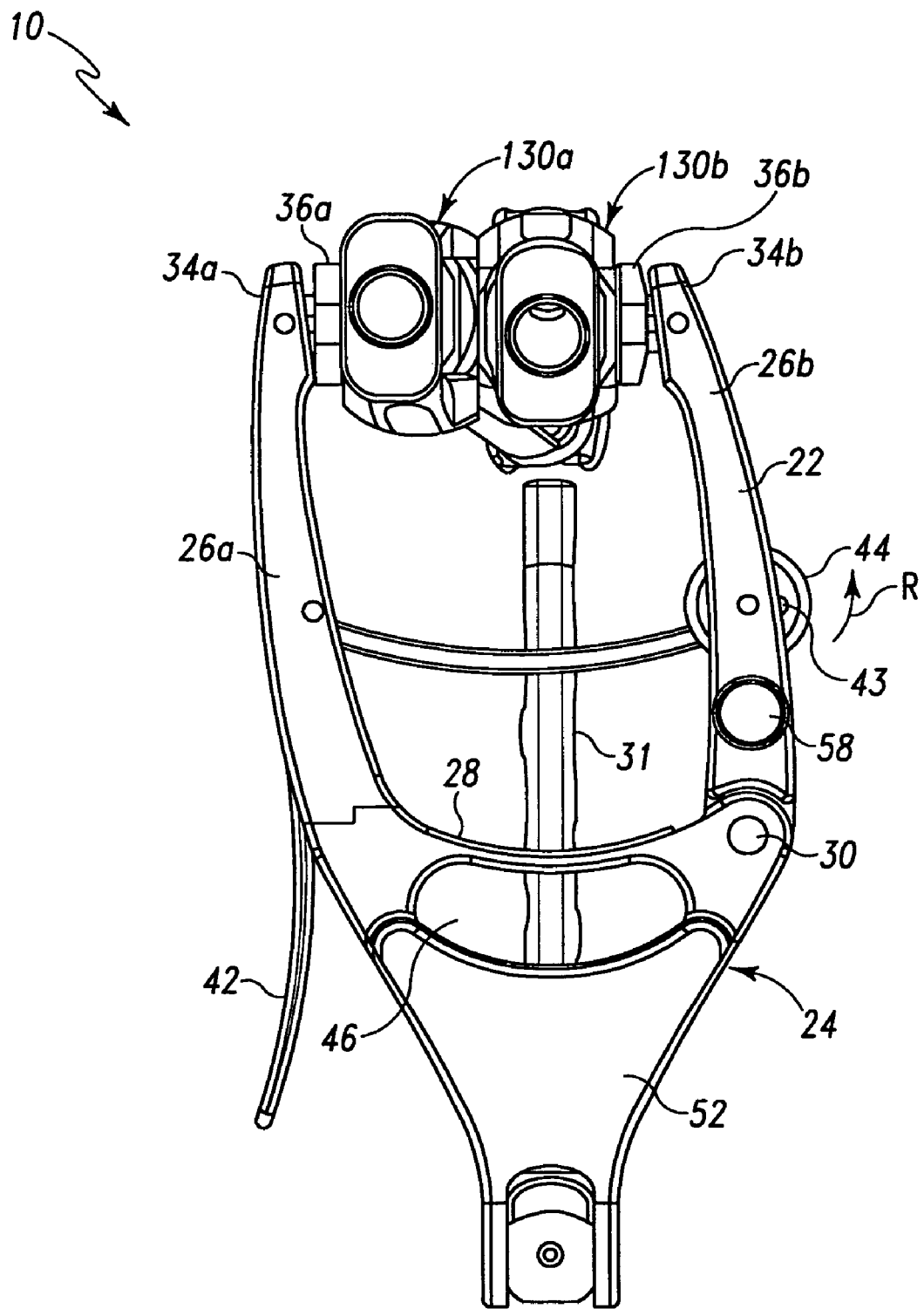
FIG. 6 is a top plan view of the inserter clamped to a pair of anchor extensions.
Figure 7:
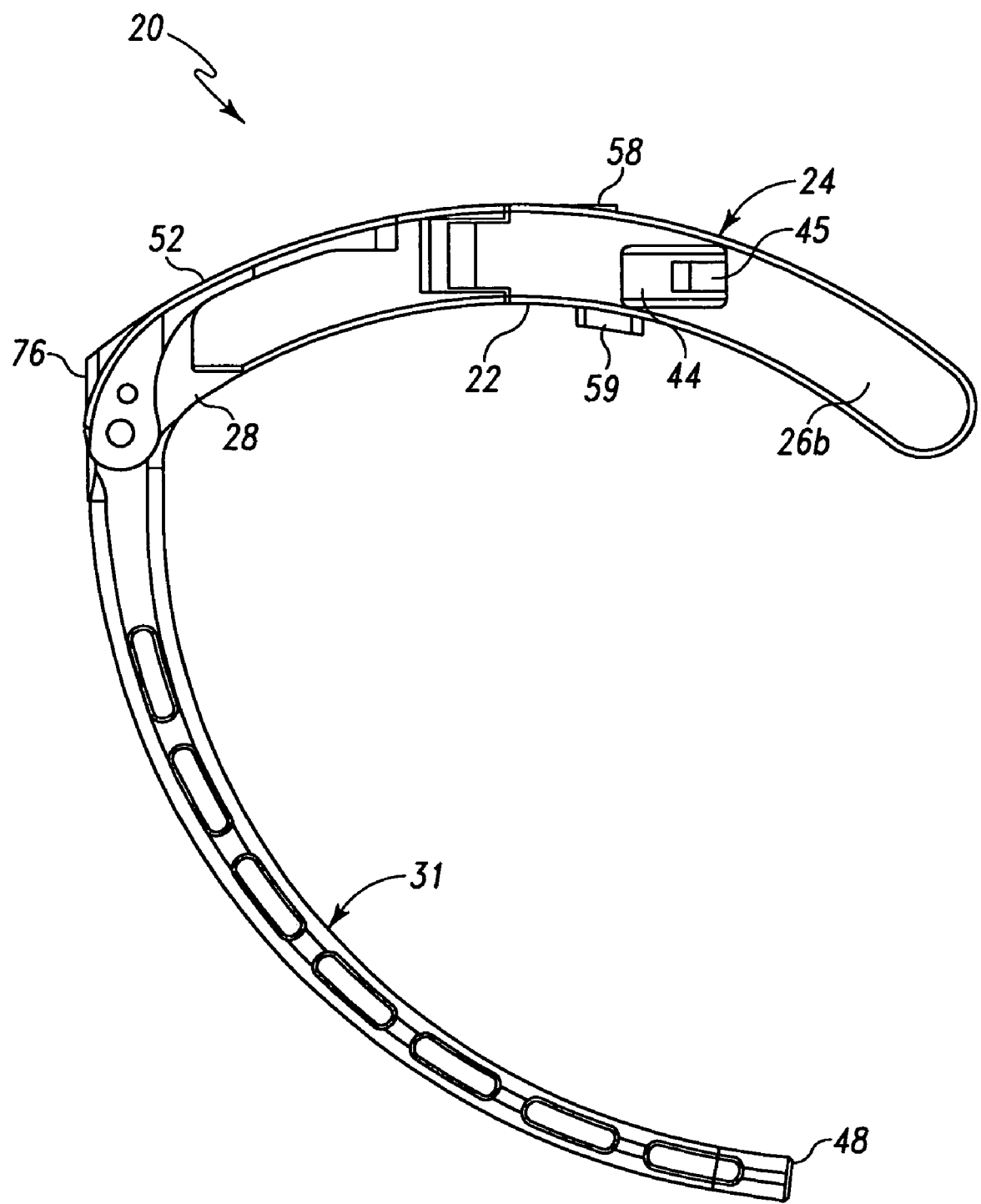
FIG. 7 is a side view of the inserter with a wheel release mechanism depressed.

The clamping assembly and pivotal movement of second arm 26b permits inserter 24 to be readily employed in procedures using three anchor extensions, as shown in FIGS. 1, 4 and 5, and procedures using two anchor extensions, as shown in FIG. 6. The spacing between support arms 26a, 26b can be adjusted to accommodate two anchor extensions by depressing release mechanism 58, as shown in FIG. 7. This displaces a wheel engaging portion 59 that is normally biased onto engagement with wheel 44 to maintain its rotational positioning. When released, wheel 44 can rotate in a direction R about its rotational connection with second support arm 26b to displace the second end of clamping arm 40 through support arm 26b to location 43 as second support arm 26b is pivoted about connection 30 toward first support arm 26a. Wheel 44 allows the effective length of clamping arm 40 between support arms 26a, 26b to be adjusted accommodate the change in spacing between support arms 26a, 26b necessary to securely clamp two anchor extensions 130 therebetween. After wheel 44 is rotated to the adjusted position, release mechanism 58 is released and re-engages wheel 44 to maintain it in the adjusted position. Other embodiments contemplate the support arms and clamping assembly can be configured to clamp about a single anchor extension, or four or more anchor extensions.

Support arms 26a, 26b come together at a junction portion 28. Junction portion 28 defines a hand-hole 46 to facilitate manual grasping of the inserter 24 and facilitates pivoting movement of it about anchor extensions 130. There is further provided an actuating member 52 pivotally coupled at junction portion 28 that operates a locking mechanism 50 to remotely secure and release the connecting element 90 to installation instrument 10. Actuating member 52 can be accessed in handle-hole 46 to pivot it between locked and unlocked positioned to selectively engage and release the connecting element 90 adjacent a distal end 48 of inserter arm 31, as discussed further below.

Figure 9:
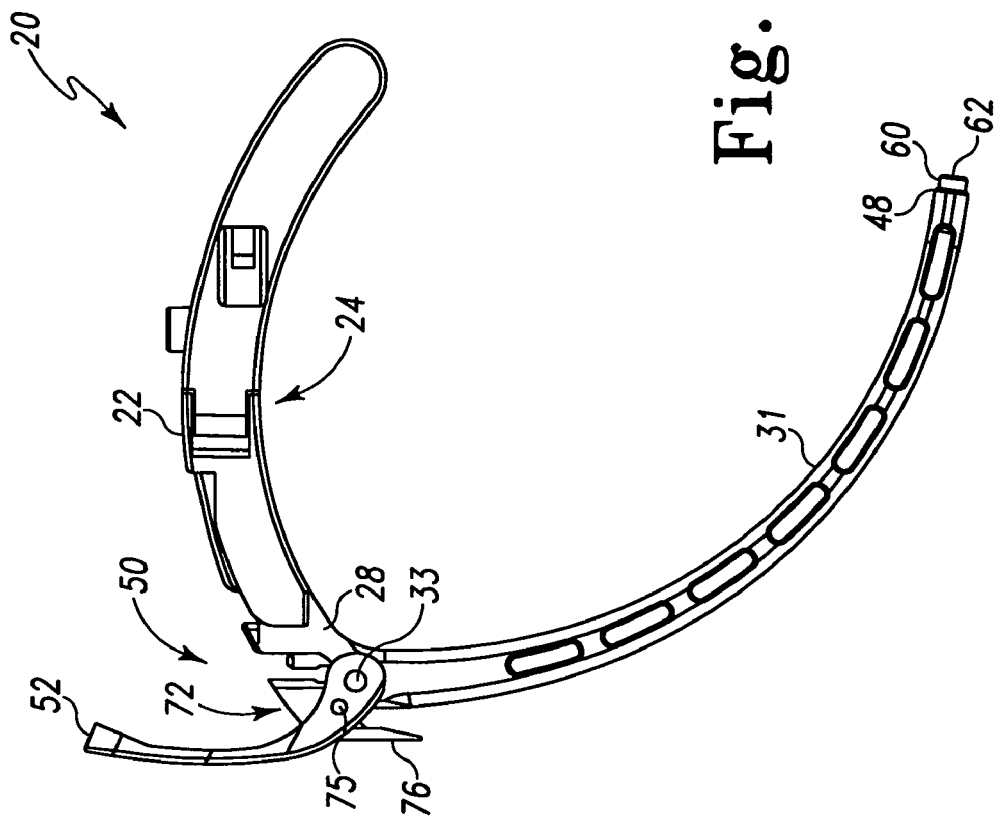
FIG. 9 is a side view of the inserter of FIG. 8.
Figure 8:
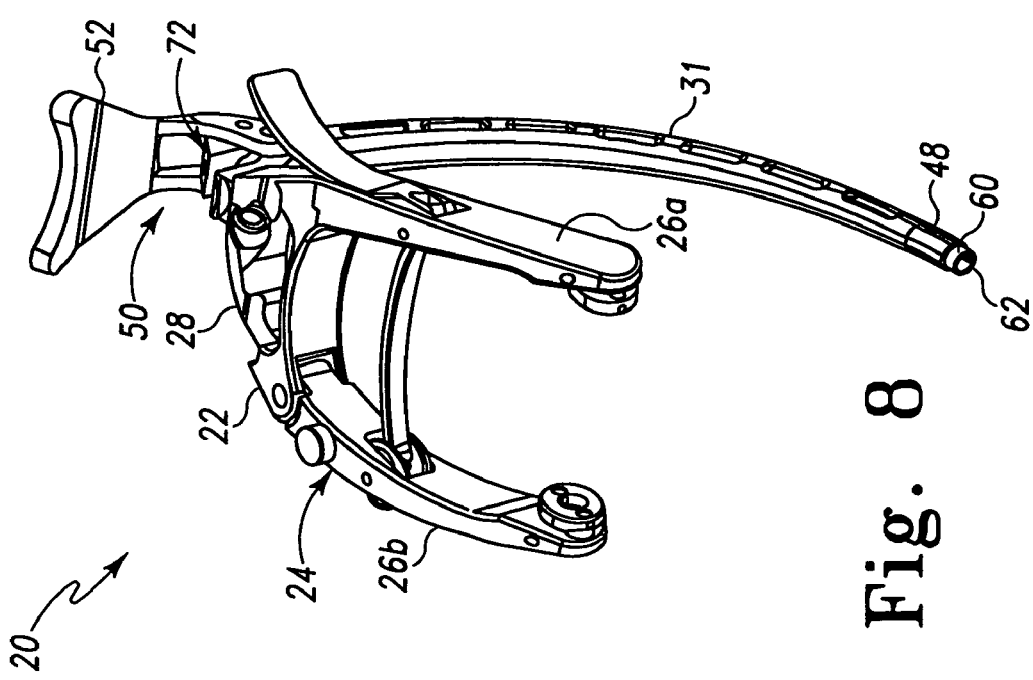
FIG. 8 is a perspective view of the inserter with an actuating member in an unlocked position.
Figure 11:
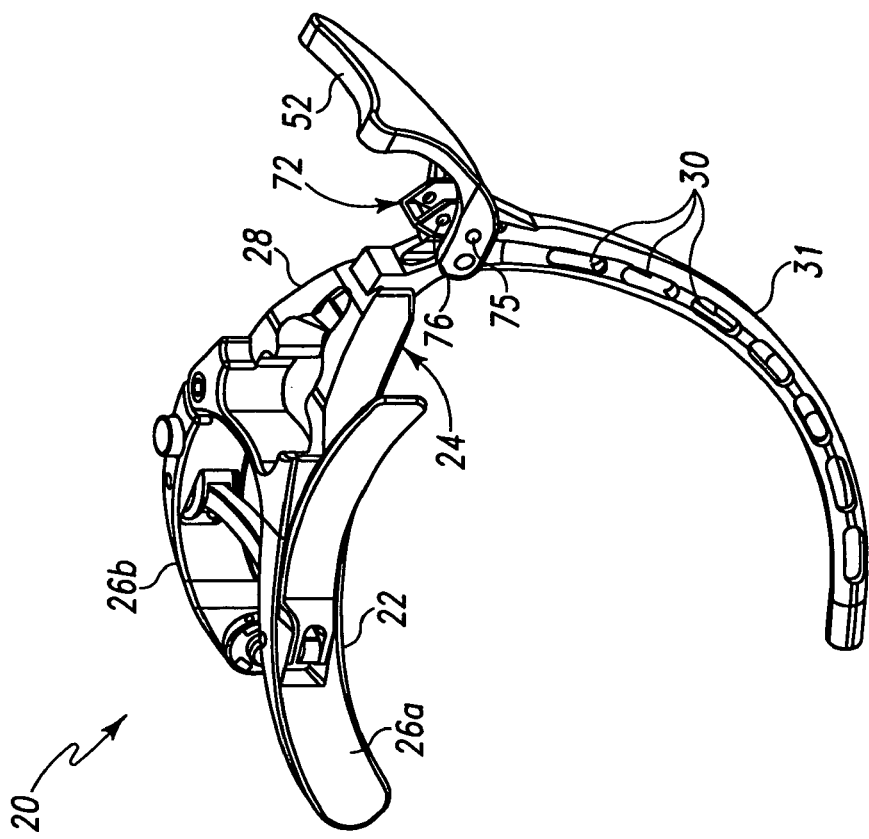
FIG. 11 is the inserter of FIG. 10 with the latch mechanism in an unlocked position.

Referring now to FIGS. 7-11, locking mechanism 50 will be discussed further. Locking mechanism 50 is shown in FIG. 7 in a locked condition and with connecting element securing member 60 removed therefrom. In FIGS. 8 and 9, the locking mechanism 50 is unlocked by pivoting actuating member 52 about its pivotal connection 33 with junction portion 28. This in turn displaces securing member 60 so that a securing end 62 extends from distal end 48 of inserter arm 31. In the unlocked position, a trailing end of connecting element 90, or some other portion of the connecting element, can be positioned in securing end 62. As actuating member 52 is moved to the locked position of FIG. 7, securing member 60 translates in bore 78 of inserter arm 31 and draws securing end 62 therein. This in turn clamps the connecting element in securing end 62, securing it to the distal end 48 of inserter arm 31. Securing end 62 can be provided as a collet with bifurcated walls 62a, 62b as shown in FIG. 12 or other radially expandable and contractable structure to grippingly engage connecting element 90 thereto.

Further details of securing member 60 are shown in FIGS. 12-14. Securing member 60 includes an elongated body 64 extending from securing end 62 to a latching end 66. A reduced cross-section portion 68 is provided adjacent latching end 66 to allow additional flexibility thereto, for reasons discussed further below. Latching end 66 includes opposite notches 70a, 70b positioned below an enlarged head portion 69. Notches 70a, 70b receiving a latching mechanism 72 to releasably couple securing member 60 in inserter arm 31, as discussed further below.

Figure 10:
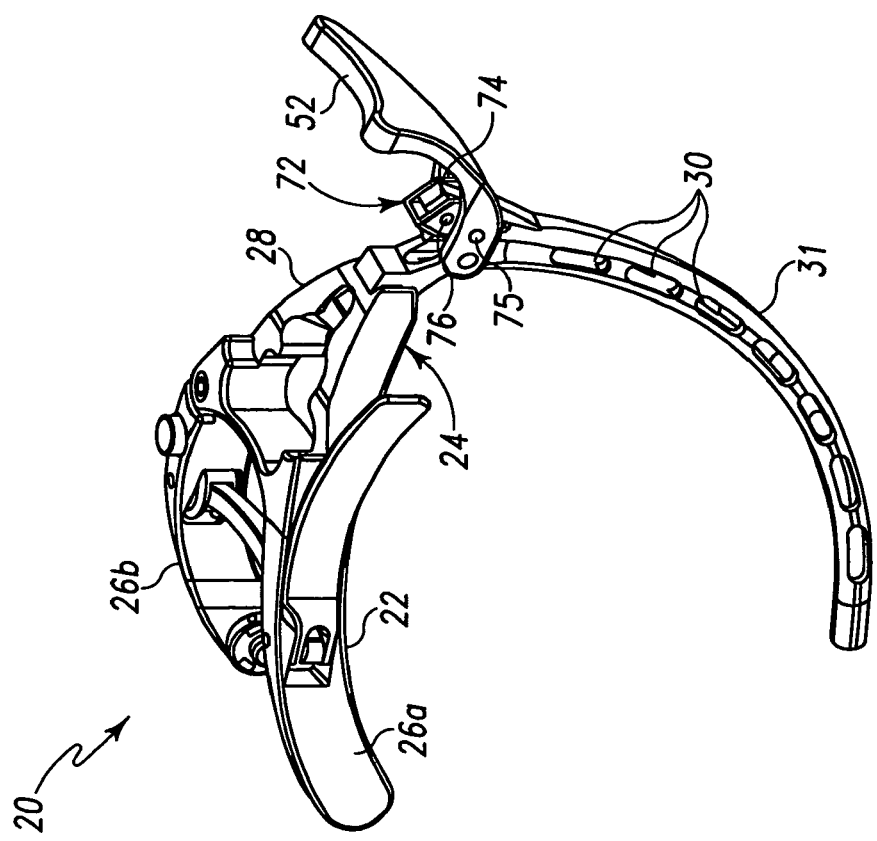
FIG. 10 is another perspective view of the inserter with the actuating member in an unlocked position and a latch mechanism in a locked position.

FIG. 10 shows a latching mechanism 72 comprising a portion of locking mechanism 50 in a latched position. Latching mechanism 72 includes a housing 76 and a latch member 74. Latch member 74 is movable relative to housing 76 between the latched position and an unlatched position shown in FIG. 11. In the latched position, latch member 74 engages head portion 69 and locks securing member 60 in inserter arm 31. In the unlatched position, securing member 60 can be moved relative to inserter arm 31 to position head portion 69 into and out of housing 76. This allows securing member 60 to be removed for sterilization after a surgical procedure, or to allow replacement of securing member 60 without replacement of the entire inserter 24. Furthermore, instrument 20 can be sterilized more effectively with securing member 60 removed since bore 78 of inserter arm 31 is unobstructed, facilitating removal of any biomaterial that may be trapped therein. Sidewall holes 30 in inserter arm 31 are in communication with the central bore 78 thereof, further facilitating cleaning and sterilization.

Figure 16:
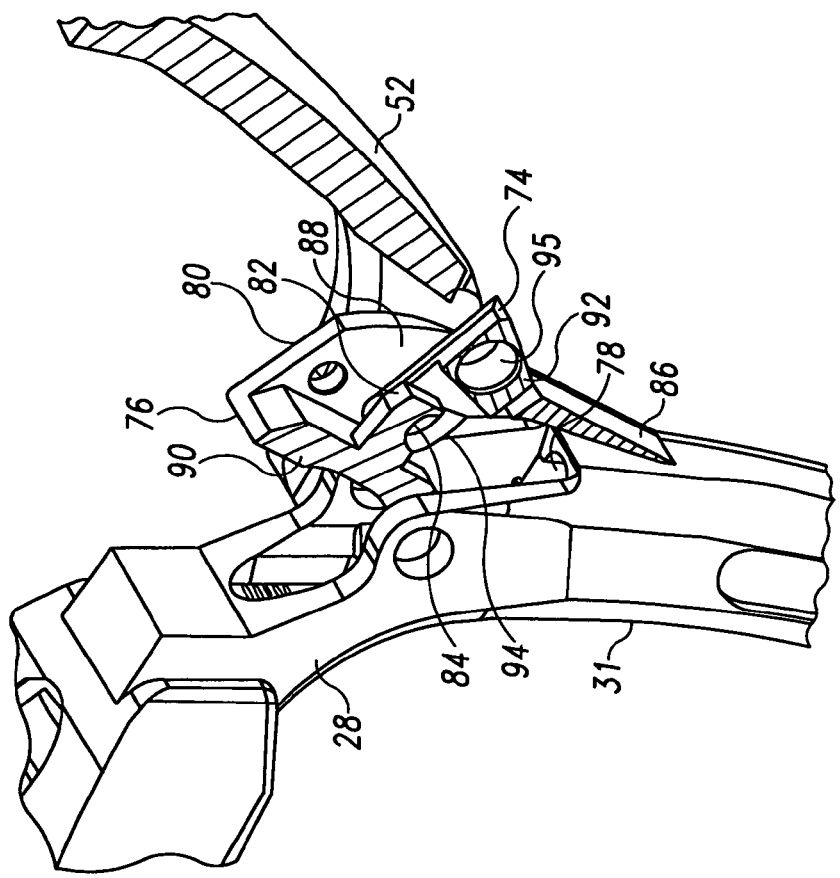
FIG. 16 is the view of FIG. 15 with the latch mechanism in an unlatched position.
Figure 15:
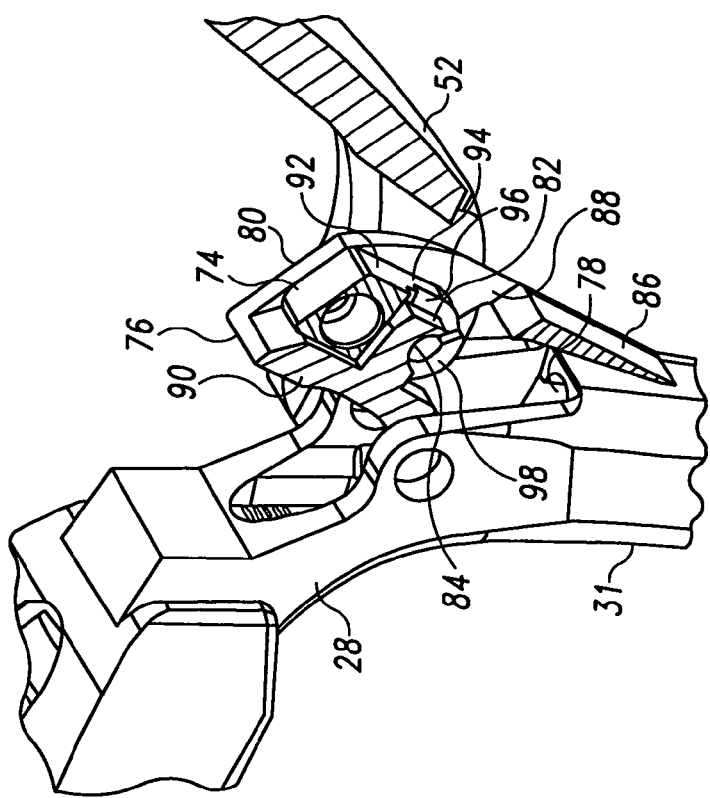
FIG. 15 is a partial perspective view in partial section of the latch mechanism of the inserter in a latched position.

FIGS. 15 and 16 show latching mechanism 72 in further detail. Housing 76 is pivotally coupled to actuating member 52 at connection 75, as shown in FIG. 9. Housing 76 includes sidewalls 80 forming a central slot 88 therebetween. A lower extension 86 extends between sidewalls 80 adjacent a frontal end thereof and adjacent a lower end of slot 88. An inner wall 90 extends between sidewalls 80 along an inner side of housing 76. A central projection 82 extends from inner wall 90 centrally between sidewalls 80, forming a space between each of the sidewalls 80 and projection 82.

Latch member 74 includes an upper portion 92 and an integral lower latching end 94. Upper portion 92 includes a through-hole 95 to receive a pin (not shown) to secure latch member 74 to housing 76 when in the locked position. Lower latching end 94 is pivotally coupled to housing 76, and includes opposing arms that straddle central projection 82. The arms of latching end 94 include a space therebetween that defines a receiving portion 96 along a portion thereof, and latching projections 98 adjacent to receiving portion 96.

Figure 17A:
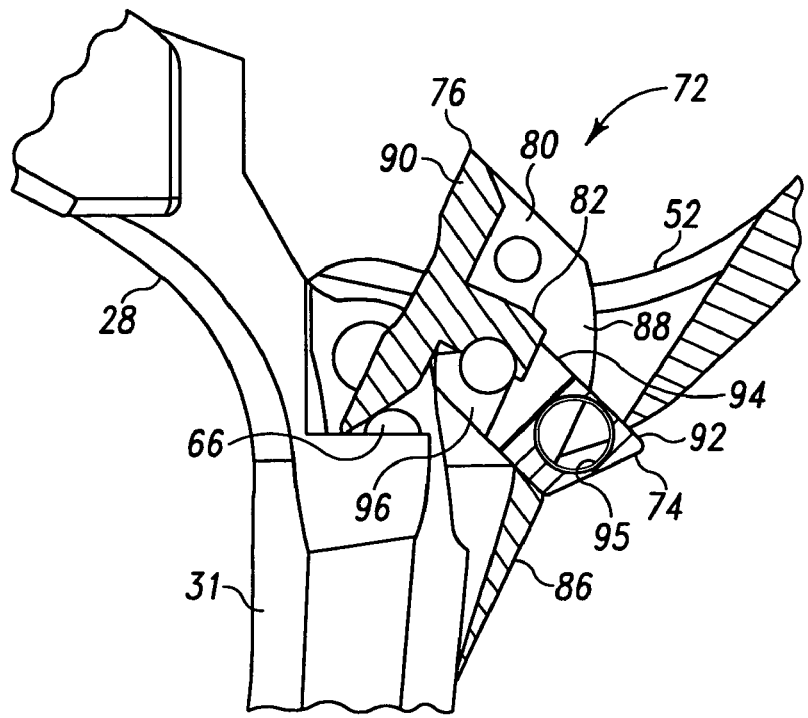
FIGS. 17A-17D show the latch mechanism in partial section and steps for locking the securing member to the latch mechanism.
Figure 17B:
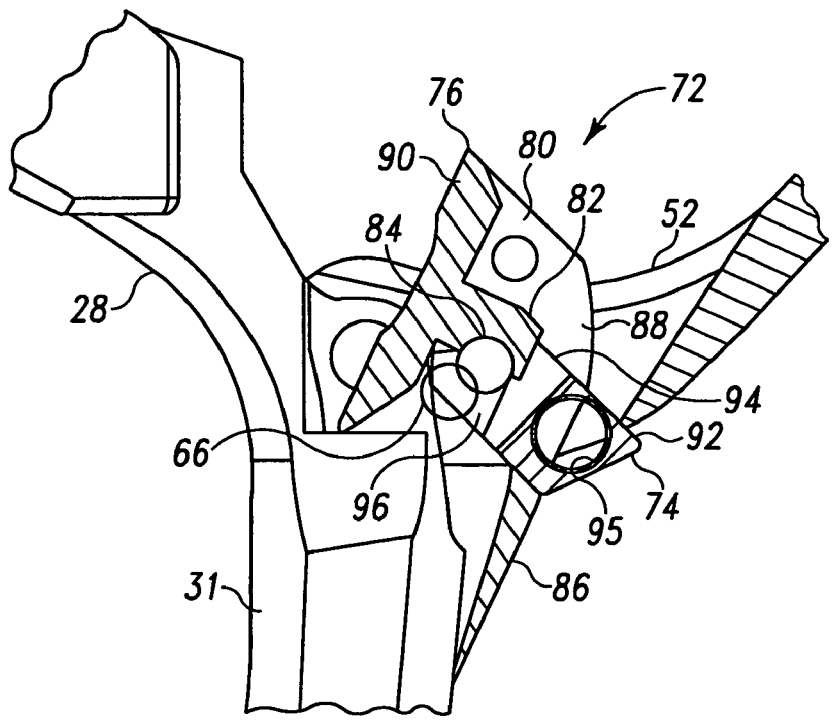

FIGS. 17A-17D show sequential steps of locking securing member 60 in latching mechanism 72. The upper end 66 of securing member 60 is shown diagrammatically in FIGS. 17A-17D. In FIG. 17A, upper end 66 projects from bore 78 of inserter arm 31, and in FIG. 17B is advanced toward central projection 82 of housing 76. The relative positioning between latch member 74 and housing 76 aligns receiving portion 96 with recess 84 of central projection 82 in the unlatched position. Receiving portion 96 is sized to allow passage of enlarged head 69 therethrough.

Figure 17C:
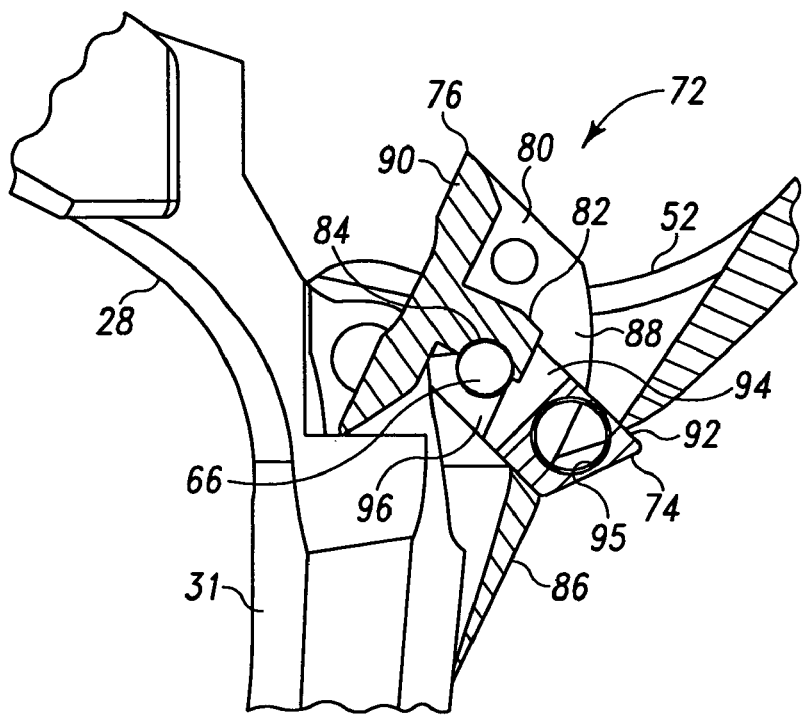
Figure 17D:
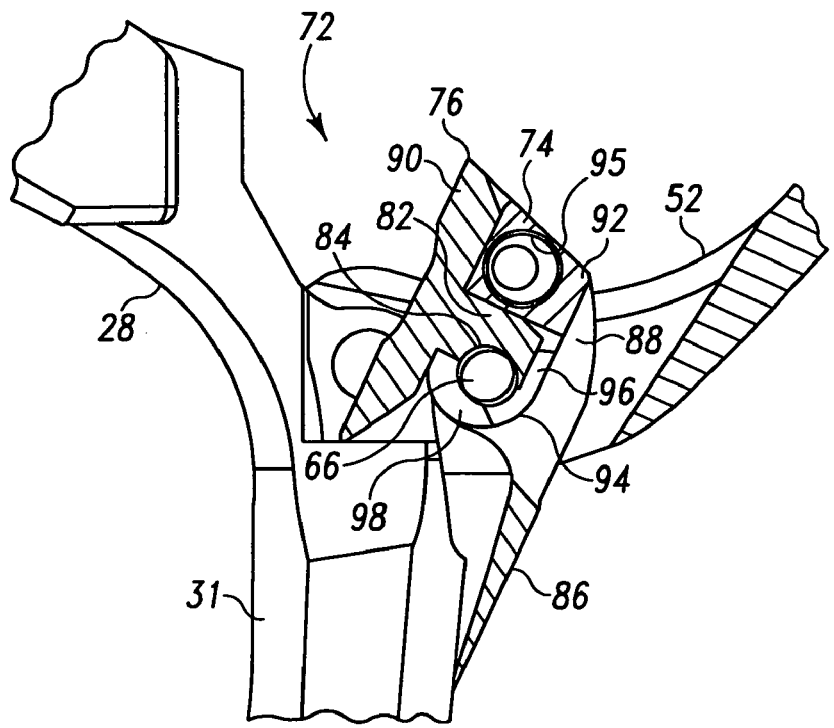

In FIG. 17C, upper end 66 of securing member 60 is seated in contact with or adjacent to central projection 82 in recess 84. Latch member 74 can then be rotated to the locked position shown in FIG. 17D. As latch member 74 is rotated, latching projections 98 are received in notches 70a, 70b formed in the underside of enlarged head 69. Latching projections 98 capture securing member 60 in latching mechanism 72. A pin (not shown) can be positioned through holes 95 of latch member 74 and engaged to housing 76 to secure latch member 74 in the latched position. If disassembly of securing member 60 is desired, the steps are reversed, and securing member 60 can be pulled through bore 78 of inserter arm 31 for removal therefrom.

Once securing member 60 is locked in position with latching mechanism 72, securing end 62 projects from distal end 48 of inserter arm 31 as shown in FIGS. 8, 9. The connecting element 90 can be positioned in securing end 62, and actuating member 52 is pivoted from its unlocked position, as shown in FIGS. 8-9, to its locked position, such as shown in FIG. 1, to securely engage connecting element 90 to inserter arm 31. The connection of housing 76 to actuating member 52 allows housing 76, and thus securing member 60, to follow actuating member 52 as it is moved between its locked and unlocked positions.

As can be seen in FIGS. 1 and 7, for example, actuating member 52 is contoured to conform to the body of inserter 24 when in the locked position to provide a low profile configuration and minimize or eliminate protrusions or abrupt edges that may interfere with the operation of installation instrument 20. Furthermore, housing 76 is formed so that it lies flush with the outer surface of inserter arm 31 when actuating member 52 is moved to the locked position, as shown in FIGS. 1 and 7, for example.

Referring now to FIGS. 18-20C, one embodiment of anchor extensions 130 will now be described in further detail. Anchor extension 130 includes an outer sleeve 132 extending along an elongated body 134. Elongate body 134 includes elongated slots 136, 137 opening along opposite sides thereof. Slots 136, 137 extend between a proximal end 139 and a distal end 138. Body 134 includes a length extending from a distal end portion 140 to an enlarged proximal end portion 142. Proximal end portion 142 includes opposite flat wall surfaces 144 to facilitate positioning of adjacent extensions 130 in side-by-side relation while minimizing the overall width of the assembled extensions 130. Rounded wall surfaces 146 extend between flat wall surfaces 144.

Anchor extension 130 further includes an inner sleeve 150 positioned in a bore extending through outer sleeve 132. Inner sleeve 150 includes a tubular body 158 defining distal fingers 154, 155. Fingers 154, 155 are separated by a slot to facilitate fingers 154, 155 moving toward and away from another to capture anchor 100 therebetween. Fingers 154, 155 include flanged ends 164, 165, respectively, at their distal ends that project outwardly for abutting engagement with distal end portion 140 of outer sleeve 132. Flanged ends 164, 165 further each include a projection or nub 166 (only one shown) that engage an adjacent recess in anchor 100 to facilitate securely mounting anchor extension 130 to anchor 100.

Fingers 154, 155 also each include a projecting member 152, 153, respectively, extending therefrom through respective ones of the slots 136, 137. Projecting members 152, 153 contact the distal end 138 of slots 136, 137 to limit the proximal displacement of outer sleeve 132 relative to inner sleeve 150, as shown in FIGS. 20A and 20B. In this open position, fingers 154, 155 are spaced from one another to receive anchor 100 therebetween. In FIG. 20C, outer sleeve 132 is advanced distally along fingers 154, 155 to bias flanged ends 164, 165 into engagement with anchor 100. The outer surfaces of fingers 154, 155 can be ramped to provide a larger cross-section adjacent flanged ends 164, 165, facilitating positive closure of the fingers 154, 155 against anchor 100. Distal portion 140 of outer sleeve 132 can contact flanged ends 164, 165 to prevent further distal displacement of outer sleeve 132 about inner sleeve 150. The spacing 160 between the distal ends of projecting members 152, 153 and the proximal ends of flanged ends 164, 165 defines a distance along which sleeves 132, 150 move relative to one another between the open and clamping positions.

In the illustrated embodiment of FIG. 20C, anchor extension 130 is shown clampingly engaged to connecting element engaging portion 104 of anchor 100 between fingers 154, 155. The slot between the fingers 154, 155 is aligned with the passage 106 defined between arms 107, and fingers 154, 155 are aligned with and positioned about respective ones of the arms 107. Nubs 165 can be received in recesses (not shown) formed in arms 107 to further resist dislodgement of anchor 100 from anchor extension 130. In the clamped condition, bone engaging portion 102 remains free pivot relative to connecting element engaging portion 104 should anchor 100 be provided in multi-axial form.

FIGS. 19A-19C show in partial section proximal end portion 142 of anchor extension 130 and a toggle mechanism 170 that locks sleeves 132, 150 to one another in the clamping position, and that also facilitates unlocking of sleeves 132, 150 when it is desired to remove anchor extension 130 from anchor 100. Toggle mechanism 170 includes a body between sleeves 132, 150 that has a proximal gripping portion 172 and an intermediate collar 174 extending at least partially thereabout. In the locking position of FIG. 19A, toggle latches 176 engage collar 174. A distal portion 178 of toggle mechanism 170 includes a proximally oriented taper that extends from a distal end 179 toward the proximal end.

Buttons 180 are pivotally coupled to proximal end portion 142 of outer sleeve 132 with pins 182. Buttons 180 extend from a distal end 184 to a proximal end 186. Distal ends 184 are biased away from outer sleeve 132 with respective button springs 188. Proximal ends 186 each include a V-shaped recess 190 that interdigitates with a correspondingly shaped recess 192 of the adjacent toggle latch 176. Toggle latch 176 includes a lip 194 that engages a proximally oriented surface of collar 174 in the locked condition. This engagement locks toggle mechanism 170 in position relative to inner sleeve 150 and outer sleeve 132, preventing toggle mechanism 170 from being displaced proximally therefrrom.

Toggle mechanism 170 further includes sleeve latches 200 positioned between respective ones of the toggle buttons 180 and extending therethrough to inner sleeve 150. Sleeve latches 200 each include a projection 204 forming a proximally oriented lip that, in the locked position, is received in an adjacent notch 158 formed in the outer surface of inner sleeve 150. Latch springs 202 bias the respective sleeve latches 200 toward inner sleeve 150 to maintain the locked condition between sleeves 132, 150 when latch springs 202 are aligned with notches 158. Sleeve latches 200 include an inner surface 201 positioned along and in contact with tapered distal portion 178 of toggle mechanism 170.

Figure 18:
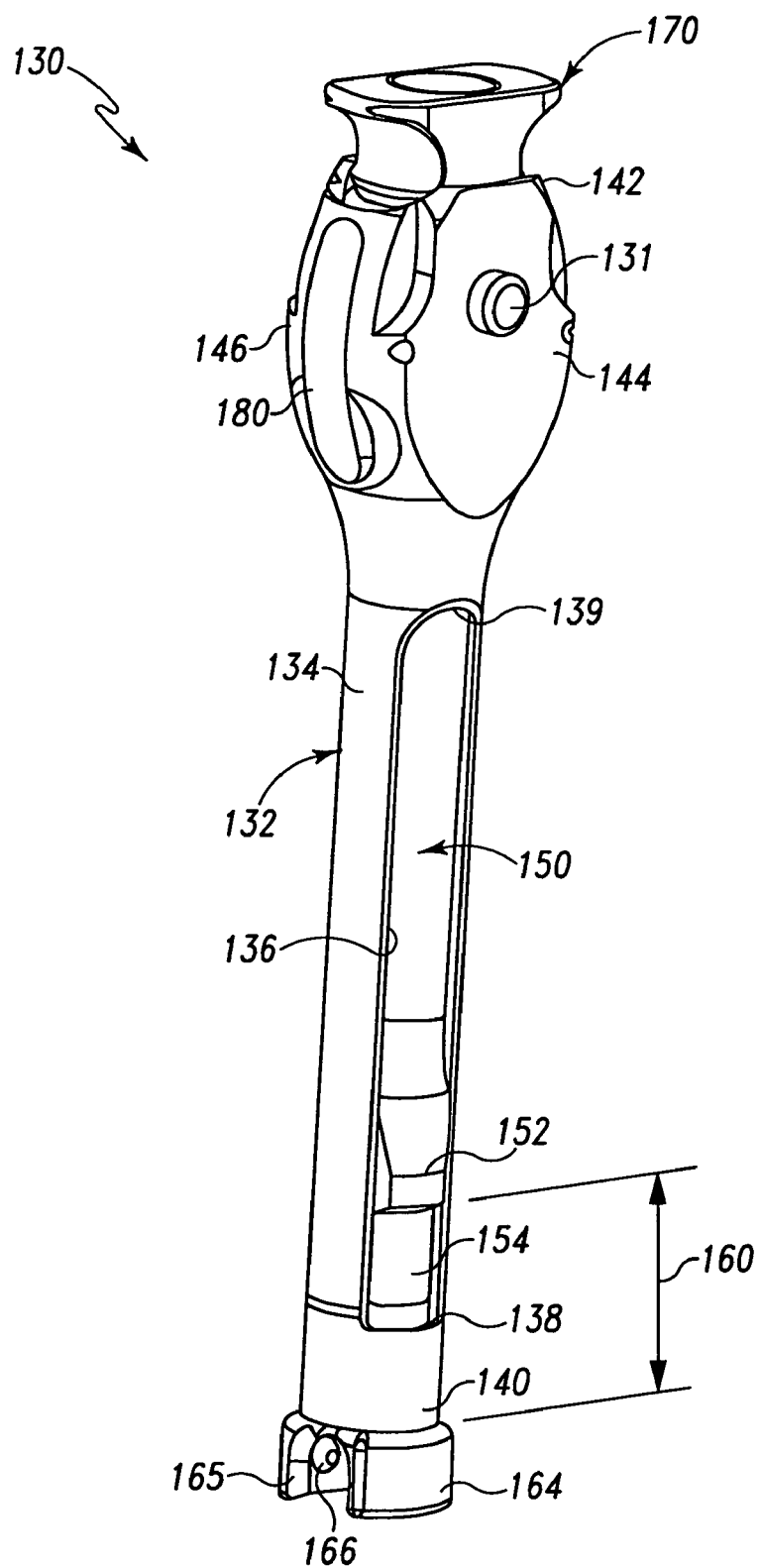
FIG. 18 is a perspective view of an anchor extension comprising a portion of the system of FIG. 1.

In FIG. 19A, sleeves 132, 150 are locked relative to one another in the clamping position (as shown in FIGS. 18 and 20C) to prevent sleeves 132, 150 from being moved relative to one another. In order to unlock outer sleeve 132 from inner sleeve 150, buttons 180 are pressed against the bias of button springs 188, causing proximal ends 186 to rotate about the respective pins 182. This in turn displaces toggle latches 176 away from collar 174 until lip 194 is no longer engaged therewith. This allows proximal gripping portion 172 to be pulled proximally along the longitudinal axis 139 of anchor extension 130 to displace toggle mechanism 170 relative to inner sleeve 150 and outer sleeve 132.

As toggle mechanism 170 is proximally displaced relative to sleeves 132, 150, distal ramped portion 178 acts to displace sleeve latches 200 away from inner sleeve 150. The ramped surfaces of tapered portion 178 gradually compress button springs 202 until projections 204 are displaced out of the respective notches 158. When projections 204 are completely removed from notches 158, outer sleeve 132 is free to slide proximally relative to inner sleeve 150 until distal end portion 140 contacts projecting members 152, 153. Fingers 154, 155 are then free to move away from one another a sufficient amount to receive anchor 100 therebetween or to release an anchor 100 secured therebetween.

Various surgical techniques can be completed with the system 10. One type of surgical technique is directed to spinal surgery for positioning an elongated connecting element along one or more vertebral levels to provide spinal stabilization. A number of anchors 100 are selected according to the number of vertebral levels to be instrumented. For example, a single level procedure may include an anchor engaged to each of two vertebrae, or a two level procedure may include an anchor engaged to each of three vertebrae.

When the desired number of levels has been selected, anchors 100 can be engaged to the respective vertebrae. In posterior spinal surgical techniques, the anchors 100 can be screws engaged in the pedicles of the vertebrae. Anchors 100 can be positioned into the patient through one or more minimally invasive access portals, formed by an incision, cannula, or retractor system, for example. The anchor extensions can be clamped to the anchors after the anchors are engaged to the vertebrae. Alternatively, the anchors can be clamped to the extensions, and then delivered through the access portal or portals for engagement with the respective vertebrae. Placement of the anchors can be facilitated using a guidewire, image guided surgery system, fluoroscopic imaging, X-rays, CT scans, endoscopic viewing systems, microscopic viewing systems, loupes, and/or naked eye visualization, for example.

With the anchors 100 engaged to the vertebrae and with extensions 130 extending therefrom, extensions 130 have a length sufficient to extend from the patient so that their proximal ends are accessible for mounting inserter 24 thereto. Extensions 130 are manipulated so that their proximal ends are placed in side-by-side relation, and mounting portion 22 of inserter 24 is positioned so that arms 26 can be manipulated to engage one, two, or three more extensions 130 therebetween. Connecting element 90 can be engaged to inserter arm 31 if not already so engaged. Inserter 24 can then be pivoted about the proximal ends of extensions 130 to place connecting element 90 to a location adjacent anchors 100.

Prior to placement of connecting element 90, a trocar can be engaged to inserter 24 and moved into the patient by pivoting inserter 24 about extensions 130 along the insertion axis I from a location outside the patient, through skin and/or tissue of the patient, and to anchors 100. Inserter 24 can be pivoted in the reverse direction to withdraw the trocar. The trocar can then be removed, and connecting element 90 engaged to the inserter 24 to move it along insertion path I formed in the patient by the trocar until the connecting element extends between anchor 100 and to the connecting element engaging portions 104 thereof. It is further contemplated that the leading end of connecting element 90 can be tapered or pointed to facilitate puncture and/or tunneling through the skin and tissue of the patient, either to form a path or to be inserted along a path formed by a trocar. Placement of the connecting element 90 can be monitored and/or confirmed using any of the visualization techniques discussed above.

Connecting element 90 can be remotely disengaged from inserter arm 31 by manipulating actuating member 52 to release securing end 62 of securing member 60 from connecting element 90. Inserter 24 can then be withdrawn from the patient by pivoting it about extensions 130 in the reverse direction. Set screws or other securing members can be delivered through extensions 130 with a driving instrument, and engaged with respective ones of the anchors 100 to secure connecting element 90 to anchors 100. Extensions 100 can then be unclamped from the respective anchors 100 by manipulating toggling mechanism 170 as discussed above.

One or more other connecting elements can be similarly engaged to the spinal column along the same vertebral level or levels, or along other vertebral levels. Other procedures can also be completed in conjunction with the stabilization procedure, including discectomy, interbody fusion, artificial disc replacement, bone removal, tissue removal, intravertebral reduction, joint replacement, annular repair, and/or any other spinal surgical procedures.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A system for minimally invasive surgical procedures in a patient, comprising:
    a number of anchor extensions each including an elongated body extending between a distal end and a proximal end, said body having a length wherein when said distal end is mounted to at least one anchor for engagement to bony structure of the patient and said proximal end is located outside the patient;
    a connecting element for implantation in the body of the patient; and
    an installation instrument including a mounting portion engageable to said number of anchor extensions and an inserter arm extending from said mounting portion along an axis oriented transversely to said mounting portion, said inserter arm including a bore with an elongated securing member therein, said securing member extending between a securing end adjacent a distal end of said inserter arm and an opposite end coupled to an actuating member adjacent a proximal end of said inserter arm, said actuating member being pivotally mounted to said installation instrument for movement between an unlocked positioned wherein said securing end projects from said distal end of said inserter arm to receive said connecting element to a locked position wherein said actuating member moves said securing end into said bore of said inserter arm, said inserter arm engaging said securing member as said securing member is moved therein to engage said connecting element to said securing end, wherein said actuating member is coupled to a latch mechanism, said latch mechanism being releasably engaged to said opposite end of said securing member, wherein when said actuating member is in said unlocked position said latch mechanism is movable between an unlatched position for receiving and removing said opposite end of said securing member therein and a latched position for engaging said opposite end of said securing member therein and said latch mechanism includes a housing mounted to said actuating member and a latch member coupled to said housing, said latch member being movable relative to said housing between said latched and unlatched position.

2. The system of claim 1, wherein said securing member includes a collet at said securing end, said inserter arm compressing said collet to engage said connecting element when said actuating member is moved to said locked position.

3. The system of claim 1, wherein said connecting element is elongated and extends between a leading insertion end and a trailing end, said securing member being engaged to said trailing end with said connecting element extending along said axis of said inserter arm.

4. The system of claim 1, wherein said opposite end of said securing member includes an enlarged head and a pair of notches between said enlarged head and a body of said securing member, said latch member including latching projections received in respective ones of said notches when said latch member is in said latched position.

5. The system of claim 4, wherein said latch member includes an upper end pivotal toward and away from said housing about a lower latching end pivotally coupled to said housing, said lower latching end including opposite fingers defining a space therebetween having an open portion sized to pass said enlarged head therethrough when in said unlatched position.

6. The system of claim 1, wherein said inserter arm includes a number of openings spaced along a length thereof between said mounting portion and said distal end, said openings being in communication with said bore of said inserter arm.

7. A system for minimally invasive surgical procedures in a patient, comprising:
    a number of anchor extensions each including an elongated body extending between a distal end and a proximal end, said body having a length wherein when said distal end is mounted to at least one anchor for engagement to bony structure of the patient and said proximal end is located outside the patient;
    a connecting element for implantation in the body of the patient; and
    an installation instrument including a mounting portion engageable to said number of anchor extensions and an inserter arm extending from said mounting portion along an axis oriented transversely to said mounting portion, said inserter arm including an elongated securing member therein, said securing member extending between a securing end adjacent a distal end of said inserter arm and an opposite end coupled to a latch mechanism at a proximal end of said inserter arm, wherein said latch mechanism includes a housing mounted to said installation instrument and a latch member coupled to said housing, said latch member being movable relative to said housing between an unlatched position to permit said opposite end of said securing member to be inserted into and withdrawn from said housing and a latched position wherein said latch member locks said opposite end in said housing, wherein said latch mechanism is coupled to an actuating member, said actuating member being pivotally mounted to said installation instrument for movement of said securing member between an unlocked positioned wherein said securing end of said securing member projects from said distal end of said inserter arm to receive said connecting element and a locked position wherein said securing end is moved into said bore of said inserter arm, said inserter arm engaging said securing member as said securing member is moved therein to engage said connecting element to said securing end.

8. The system of claim 7, wherein said opposite end of said securing member includes an enlarged head and a pair of notches between said enlarged head and a body of said securing member, said latch member including latching projections received in respective ones of said notches when said latch member is in said latched position.

9. The system of claim 8, wherein said latch member includes an upper end pivotal toward and away from said housing about a lower latching end pivotally coupled to said housing, said lower latching end including arms defining a space therebetween having a receiving portion sized to receive said enlarged head therethrough when said latch member is in said unlatched position, said latching projections being adjacent said receiving portion for positioning in said notches as said latch member is pivoted to said latched position.

* * * * *